US010395097B2

United States Patent
Hanna

(10) Patent No.: US 10,395,097 B2
(45) Date of Patent: *Aug. 27, 2019

(54) METHOD AND SYSTEM FOR BIOMETRIC RECOGNITION

(71) Applicant: EyeLock LLC, New York, NY (US)

(72) Inventor: Keith J. Hanna, New York, NY (US)

(73) Assignee: Eyelock LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/962,629

(22) Filed: Apr. 25, 2018

(65) Prior Publication Data

US 2019/0005307 A1   Jan. 3, 2019

Related U.S. Application Data

(63) Continuation of application No. 15/589,752, filed on May 8, 2017, now Pat. No. 9,959,478, which is a
(Continued)

(51) Int. Cl.
| | | |
|---|---|---|
| *G06K 9/00* | (2006.01) | |
| *A61B 5/117* | (2016.01) | |
| *H04N 5/225* | (2006.01) | |
| *H04N 5/232* | (2006.01) | |
| *H04N 5/235* | (2006.01) | |

(Continued)

(52) U.S. Cl.
CPC ........ *G06K 9/00255* (2013.01); *A61B 5/117* (2013.01); *G06F 21/32* (2013.01); *G06K 9/00248* (2013.01); *G06K 9/00261* (2013.01); *G06K 9/00288* (2013.01); *G06K 9/00604* (2013.01); *G06K 9/00617* (2013.01); *G06K 9/00892* (2013.01); *G06K 9/3208* (2013.01); *G06T 7/521* (2017.01); *G06T 7/74* (2017.01);
(Continued)

(58) Field of Classification Search
CPC .......... G06K 9/00255; G06K 9/00248; G06K 9/00261; G06T 7/74; G06T 7/521
See application file for complete search history.

(56) References Cited

U.S. PATENT DOCUMENTS

| 4,641,349 A | 2/1987 | Flom et al. |
|---|---|---|
| 5,259,040 A | 11/1993 | Hanna |

(Continued)

FOREIGN PATENT DOCUMENTS

| KR | 102002007822 | 10/2002 |
|---|---|---|
| KR | 102003000511 | 1/2003 |

(Continued)

OTHER PUBLICATIONS

B. Galvin, et al., Recovering Motion Fields: An Evaluation of Eight Optical Flow Algorithms, Proc. of the British Machine Vision Conf. (1998) (pp. 195-204).
(Continued)

*Primary Examiner* — Gregory M Desire
(74) *Attorney, Agent, or Firm* — Foley & Lardner LLP

(57) ABSTRACT

High quality, high contrast images of an iris and the face of a person are acquired in rapid succession in either sequence by a single sensor and one or more illuminators, preferably within less than one second of each other, by changing the data acquisition settings or illumination settings between each acquisition.

20 Claims, 2 Drawing Sheets

Related U.S. Application Data continuation of application No. 14/657,415, filed on Mar. 13, 2015, now Pat. No. 9,464,217, which is a continuation of application No. 13/787,369, filed on Mar. 6, 2013, now abandoned, which is a continuation of application No. 12/596,019, filed on Oct. 15, 2009, now Pat. No. 8,953,849, which is a continuation of application No. PCT/US2008/060791, filed on Apr. 18, 2008.

(60) Provisional application No. 60/925,259, filed on Apr. 19, 2007.

(51) Int. Cl.
*G06K 9/32* (2006.01)
*G06T 7/73* (2017.01)
*G06T 7/521* (2017.01)
*G06F 21/32* (2013.01)

(52) U.S. Cl.
CPC ......... *H04N 5/2256* (2013.01); *H04N 5/2352* (2013.01); *H04N 5/23296* (2013.01)

(56) References Cited

U.S. PATENT DOCUMENTS

| | | |
|---|---|---|
| 5,291,560 A | 3/1994 | Daugman |
| 5,488,675 A | 1/1996 | Hanna |
| 5,572,596 A | 11/1996 | Wildes et al. |
| 5,581,629 A | 12/1996 | Hanna et al. |
| 5,613,012 A | 3/1997 | Hoffman et al. |
| 5,615,277 A | 3/1997 | Hoffman |
| 5,737,439 A | 4/1998 | Lapsley et al. |
| 5,751,836 A | 5/1998 | Wildes et al. |
| 5,764,789 A | 6/1998 | Pare et al. |
| 5,802,199 A | 9/1998 | Pare et al. |
| 5,805,719 A | 9/1998 | Pare et al. |
| 5,838,812 A | 11/1998 | Pare et al. |
| 5,901,238 A | 5/1999 | Matsushita |
| 5,953,440 A | 9/1999 | Zhang et al. |
| 5,978,494 A | 11/1999 | Zhang |
| 6,021,210 A | 2/2000 | Camus et al. |
| 6,028,949 A | 2/2000 | McKendall |
| 6,055,322 A | 4/2000 | Salganicoff et al. |
| 6,064,752 A | 5/2000 | Rozmus et al. |
| 6,069,967 A | 5/2000 | Rozmus et al. |
| 6,088,470 A | 7/2000 | Camus et al. |
| 6,144,754 A | 11/2000 | Okano et al. |
| 6,192,142 B1 | 2/2001 | Pare et al. |
| 6,246,751 B1 | 6/2001 | Bergl et al. |
| 6,247,813 B1 | 6/2001 | Kim et al. |
| 6,252,977 B1 | 6/2001 | Salganicoff et al. |
| 6,289,113 B1 | 9/2001 | McHugh et al. |
| 6,366,682 B1 | 4/2002 | Hoffman et al. |
| 6,373,968 B2 | 4/2002 | Okano et al. |
| 6,377,699 B1 | 4/2002 | Musgrave et al. |
| 6,424,727 B1 | 7/2002 | Musgrave et al. |
| 6,483,930 B1 | 11/2002 | Musgrave et al. |
| 6,532,298 B1 | 3/2003 | Cambier et al. |
| 6,542,624 B1 | 4/2003 | Oda |
| 6,546,121 B1 | 4/2003 | Oda |
| 6,554,705 B1 | 4/2003 | Cumbers |
| 6,594,376 B2 | 7/2003 | Hoffman et al. |
| 6,594,377 B1 | 7/2003 | Kim et al. |
| 6,652,099 B2 | 11/2003 | Chae et al. |
| 6,700,998 B1 | 3/2004 | Murata |
| 6,714,665 B1 | 3/2004 | Hanna et al. |
| 6,760,467 B1 | 7/2004 | Min et al. |
| 6,819,219 B1 | 11/2004 | Bolle et al. |
| 6,850,631 B1 | 2/2005 | Oda et al. |
| 6,917,695 B2 | 7/2005 | Teng et al. |
| 6,944,318 B1 | 9/2005 | Takata et al. |
| 6,950,536 B2 | 9/2005 | Houvener |
| 6,980,670 B1 | 12/2005 | Hoffman et al. |
| 6,985,608 B2 | 1/2006 | Hoffman et al. |
| 7,007,298 B1 | 2/2006 | Shinzaki et al. |
| 7,020,351 B1 | 3/2006 | Kumar et al. |
| 7,047,418 B1 | 5/2006 | Ferren et al. |
| 7,095,901 B2 | 8/2006 | Lee et al. |
| 7,146,027 B2 | 12/2006 | Kim et al. |
| 7,152,782 B2 | 12/2006 | Shenker et al. |
| 7,248,719 B2 | 7/2007 | Hoffman et al. |
| 7,271,939 B2 | 9/2007 | Kono |
| 7,346,472 B1 | 3/2008 | Moskowitz et al. |
| 7,385,626 B2 | 6/2008 | Aggarwal et al. |
| 7,398,925 B2 | 7/2008 | Tidwell et al. |
| 7,414,737 B2 | 8/2008 | Cottard et al. |
| 7,418,115 B2 | 8/2008 | Northcott et al. |
| 7,428,320 B2 | 9/2008 | Northcott et al. |
| 7,542,590 B1 | 6/2009 | Robinson et al. |
| 7,545,962 B2 | 6/2009 | Peirce et al. |
| 7,558,406 B1 | 7/2009 | Robinson et al. |
| 7,558,407 B2 | 7/2009 | Hoffman et al. |
| 7,574,021 B2 | 8/2009 | Matey |
| 7,583,822 B2 | 9/2009 | Guillemot et al. |
| 7,606,401 B2 | 10/2009 | Hoffman et al. |
| 7,616,788 B2 | 11/2009 | Hsieh et al. |
| 7,639,840 B2 | 12/2009 | Hanna et al. |
| 7,660,700 B2 | 2/2010 | Moskowitz et al. |
| 7,693,307 B2 | 4/2010 | Rieul et al. |
| 7,697,786 B2 | 4/2010 | Camus et al. |
| 7,715,595 B2 | 5/2010 | Kim et al. |
| 7,719,566 B2 | 5/2010 | Guichard |
| 7,770,019 B2 | 8/2010 | Ferren et al. |
| 7,787,762 B2 | 8/2010 | Abe |
| 7,797,606 B2 | 9/2010 | Chabanne |
| 7,801,335 B2 | 9/2010 | Hanna et al. |
| 7,809,171 B2 | 10/2010 | Solinsky et al. |
| 7,847,688 B2 | 12/2010 | Bernard et al. |
| 7,869,627 B2 | 1/2011 | Northcott et al. |
| 7,925,059 B2 | 4/2011 | Hoyos et al. |
| 7,929,017 B2 | 4/2011 | Aggarwal et al. |
| 7,929,732 B2 | 4/2011 | Bringer et al. |
| 7,949,295 B2 | 5/2011 | Kumar et al. |
| 7,949,494 B2 | 5/2011 | Moskowitz et al. |
| 7,978,883 B2 | 7/2011 | Rouh et al. |
| 8,009,876 B2 | 8/2011 | Kim et al. |
| 8,025,399 B2 | 9/2011 | Northcott et al. |
| 8,028,896 B2 | 10/2011 | Carter et al. |
| 8,090,157 B2 | 1/2012 | Hamza et al. |
| 8,090,246 B2 | 1/2012 | Jelinek |
| 8,092,021 B1 | 1/2012 | Northcott et al. |
| 8,118,879 B2 | 2/2012 | Wilson |
| 8,132,912 B1 | 3/2012 | Northcott et al. |
| 8,159,328 B2 | 4/2012 | Luckhardt |
| 8,170,295 B2 | 5/2012 | Fujii et al. |
| 8,181,858 B2 | 5/2012 | Carter et al. |
| 8,195,044 B2 | 6/2012 | Hanna et al. |
| 8,212,870 B2 | 7/2012 | Hanna et al. |
| 8,214,175 B2 | 7/2012 | Moskowitz et al. |
| 8,233,680 B2 | 7/2012 | Bringer et al. |
| 8,243,133 B1 | 8/2012 | Northcott et al. |
| 8,260,008 B2 | 9/2012 | Hanna et al. |
| 8,279,042 B2 | 10/2012 | Beenau et al. |
| 8,280,120 B2 | 10/2012 | Hoyos et al. |
| 8,285,005 B2 | 10/2012 | Hamza |
| 8,289,390 B2 | 10/2012 | Aggarwal et al. |
| 8,306,279 B2 | 11/2012 | Hanna |
| 8,317,325 B2 | 11/2012 | Raguin et al. |
| 8,364,646 B2 | 1/2013 | Hanna et al. |
| 8,411,909 B1 | 4/2013 | Zhao et al. |
| 8,442,339 B2 | 5/2013 | Martin et al. |
| 8,443,202 B2 | 5/2013 | White et al. |
| 8,553,948 B2 | 10/2013 | Hanna |
| 8,604,901 B2 | 12/2013 | Hoyos et al. |
| 8,606,097 B2 | 12/2013 | Hanna et al. |
| 8,719,584 B2 | 5/2014 | Mullin |
| 8,818,053 B2 | 8/2014 | Hanna et al. |
| 9,336,436 B1 | 5/2016 | Dowdall |
| 9,959,478 B2 * | 5/2018 | Hanna .................. A61B 5/117 |
| 2005/0084137 A1 | 4/2005 | Kim et al. |
| 2005/0084179 A1 | 4/2005 | Hanna et al. |
| 2005/0270386 A1 | 12/2005 | Saitoh et al. |

(56) References Cited

U.S. PATENT DOCUMENTS

| | | |
|---|---|---|
| 2006/0026427 A1 | 2/2006 | Jefferson |
| 2006/0028552 A1 | 2/2006 | Aggarwal et al. |
| 2006/0073449 A1 | 4/2006 | Kumar et al. |
| 2006/0074986 A1 | 4/2006 | Mallalieu et al. |
| 2006/0274918 A1* | 12/2006 | Amantea ............ G06K 9/00604 382/117 |
| 2006/0279630 A1 | 12/2006 | Aggarwal et al. |
| 2006/0280344 A1 | 12/2006 | Kee et al. |
| 2007/0110285 A1 | 5/2007 | Hanna et al. |
| 2007/0160265 A1* | 7/2007 | Wakiyama ......... G06K 9/00604 382/117 |
| 2007/0206839 A1 | 9/2007 | Hanna et al. |
| 2007/0211922 A1 | 9/2007 | Crowley et al. |
| 2008/0122578 A1 | 5/2008 | Hoyos et al. |
| 2008/0246917 A1 | 10/2008 | Phinney et al. |
| 2008/0291279 A1 | 11/2008 | Samarasekera et al. |
| 2009/0074256 A1 | 3/2009 | Haddad |
| 2009/0097715 A1 | 4/2009 | Cottard et al. |
| 2009/0161925 A1 | 6/2009 | Cottard et al. |
| 2009/0231096 A1 | 9/2009 | Bringer et al. |
| 2009/0274345 A1 | 11/2009 | Hanna et al. |
| 2009/0278658 A1* | 11/2009 | Higashiyama ..... G06K 9/00604 340/5.82 |
| 2010/0014720 A1 | 1/2010 | Hoyos et al. |
| 2010/0021016 A1 | 1/2010 | Cottard et al. |
| 2010/0074477 A1 | 3/2010 | Fujii et al. |
| 2010/0127826 A1 | 5/2010 | Saliba et al. |
| 2010/0232655 A1 | 9/2010 | Hanna |
| 2010/0246903 A1 | 9/2010 | Cottard |
| 2010/0253816 A1 | 10/2010 | Hanna |
| 2010/0278394 A1 | 11/2010 | Raguin et al. |
| 2010/0310070 A1 | 12/2010 | Bringer et al. |
| 2011/0002510 A1 | 1/2011 | Hanna |
| 2011/0007949 A1 | 1/2011 | Hanna et al. |
| 2011/0119111 A1 | 5/2011 | Hanna |
| 2011/0119141 A1 | 5/2011 | Hoyos et al. |
| 2011/0158486 A1 | 6/2011 | Bringer et al. |
| 2011/0194738 A1 | 8/2011 | Choi et al. |
| 2011/0211054 A1 | 9/2011 | Hanna et al. |
| 2011/0277518 A1 | 11/2011 | Lais et al. |
| 2012/0127295 A9 | 5/2012 | Hanna et al. |
| 2012/0136793 A1* | 5/2012 | Valin ..................... G06Q 20/10 705/53 |
| 2012/0187838 A1 | 7/2012 | Hanna |
| 2012/0212597 A1 | 8/2012 | Hanna |
| 2012/0219279 A1 | 8/2012 | Hanna et al. |
| 2012/0239458 A9 | 9/2012 | Hanna |
| 2012/0240223 A1 | 9/2012 | Tu |
| 2012/0242820 A1 | 9/2012 | Hanna et al. |
| 2012/0242821 A1 | 9/2012 | Hanna et al. |
| 2012/0243749 A1 | 9/2012 | Hanna et al. |
| 2012/0257797 A1 | 10/2012 | Leyvand et al. |
| 2012/0268241 A1 | 10/2012 | Hanna et al. |
| 2012/0293643 A1 | 11/2012 | Hanna |
| 2012/0300052 A1 | 11/2012 | Hanna et al. |
| 2012/0300990 A1 | 11/2012 | Hanna et al. |
| 2012/0321141 A1 | 12/2012 | Hoyos et al. |
| 2012/0328164 A1 | 12/2012 | Hoyos et al. |
| 2013/0051631 A1 | 2/2013 | Hanna |
| 2013/0110859 A1 | 5/2013 | Hanna et al. |
| 2013/0162798 A1 | 6/2013 | Hanna et al. |
| 2013/0162799 A1 | 6/2013 | Hanna et al. |
| 2013/0182093 A1 | 7/2013 | Hanna |
| 2013/0182094 A1 | 7/2013 | Hanna |
| 2013/0182095 A1 | 7/2013 | Hanna |
| 2013/0182913 A1 | 7/2013 | Hoyos et al. |
| 2013/0182915 A1 | 7/2013 | Hanna |
| 2013/0194408 A1 | 8/2013 | Hanna et al. |
| 2013/0212655 A1 | 8/2013 | Hoyos et al. |
| 2013/0294659 A1 | 11/2013 | Hanna et al. |
| 2014/0064574 A1 | 3/2014 | Hanna et al. |
| 2014/0072183 A1 | 3/2014 | Hanna et al. |
| 2015/0199006 A1* | 7/2015 | He .......................... G06F 3/013 345/158 |
| 2016/0055387 A1 | 2/2016 | Hanna et al. |
| 2017/0161557 A9* | 6/2017 | Saylor .................... G01S 17/89 |
| 2019/0005307 A1* | 1/2019 | Hanna .................... A61B 5/117 |

FOREIGN PATENT DOCUMENTS

| | | |
|---|---|---|
| KR | 100373850000 | 2/2003 |
| KR | 102003003425 | 5/2003 |
| KR | 102003005197 | 6/2003 |
| KR | 200321670000 | 7/2003 |
| KR | 100416065000 | 1/2004 |
| KR | 200340273000 | 1/2004 |
| KR | 200341137000 | 1/2004 |
| KR | 200352669000 | 5/2004 |
| KR | 200355279000 | 6/2004 |
| KR | 200362032000 | 9/2004 |
| KR | 200367917000 | 11/2004 |
| KR | 102005000533 | 1/2005 |
| KR | 200383808000 | 5/2005 |
| KR | 102005005186 | 6/2005 |
| KR | 102005010244 | 10/2005 |
| KR | 200404650000 | 12/2005 |
| KR | 100572626000 | 4/2006 |
| KR | 102006008138 | 6/2007 |
| KR | 101197678000 | 10/2012 |
| KR | 101366748000 | 2/2014 |
| KR | 101374049000 | 3/2014 |
| KR | 102014002895 | 3/2014 |
| KR | 102014003980 | 4/2014 |
| KR | 102014005050 | 4/2014 |
| WO | WO-03/060814 | 7/2003 |
| WO | WO-2005/008567 A1 | 1/2005 |
| WO | WO-2008/131201 | 10/2008 |
| WO | WO-2010/062371 | 6/2010 |
| WO | WO-2011/093538 | 8/2011 |

OTHER PUBLICATIONS

International Preliminary Report on Patentability in PCT/US2008/060791 dated Oct. 20, 2009.
International Search Report in PCT/US2008/060791 dated Aug. 27, 2008.
J. R. Bergen, et al., Hierarchical Model-Based Motion Estimation, European Conf. on Computer Vision (1993) (pp. 237-252).
K. Nishino, et al., The World in an Eye, IEEE Conf. on Pattern Recognition, vol. 1, at pp. 444-451 (Jun. 2004).
Notice of Allowance on U.S. Appl. No. 12/596,019 dated Oct. 7, 2014.
Office Action on U.S. Appl. No. 12/596,019 dated Mar. 13, 2014.
Office Action on U.S. Appl. No. 13/787,369 dated Sep. 16, 2014.
R. Kumar, et al., Direct recovery of shape from multiple views: a parallax based approach, 12th IAPR Int'l Conf. on Pattern Recognition (1994)(pp. 1-5).
R. P. Wildes, Iris Recognition: An Emerging Biometric Technology, Proc. IEEE 85(9) at pp. 1348-1363 (Sep. 1997).
U.S. Notice of Allowance on U.S. Appl. No. 14/657,415 dated Mar. 20, 2017.
U.S. Notice of Allowance on U.S. Appl. No. 15/589,752 dated Dec. 26, 2017.
U.S. Office Action on U.S. Appl. No. 14/657,415 dated Oct. 14, 2016.
U.S. Office Action on U.S. Appl. No. 15/589752 dated Jun. 2, 2017.
U.S. Office Action on U.S. Appl. No. 15/589,752 dated Oct. 5, 2017.
Written Opinion of the International Searching Authority in PCT/US2008/060791 dated Aug. 27, 2008.

* cited by examiner

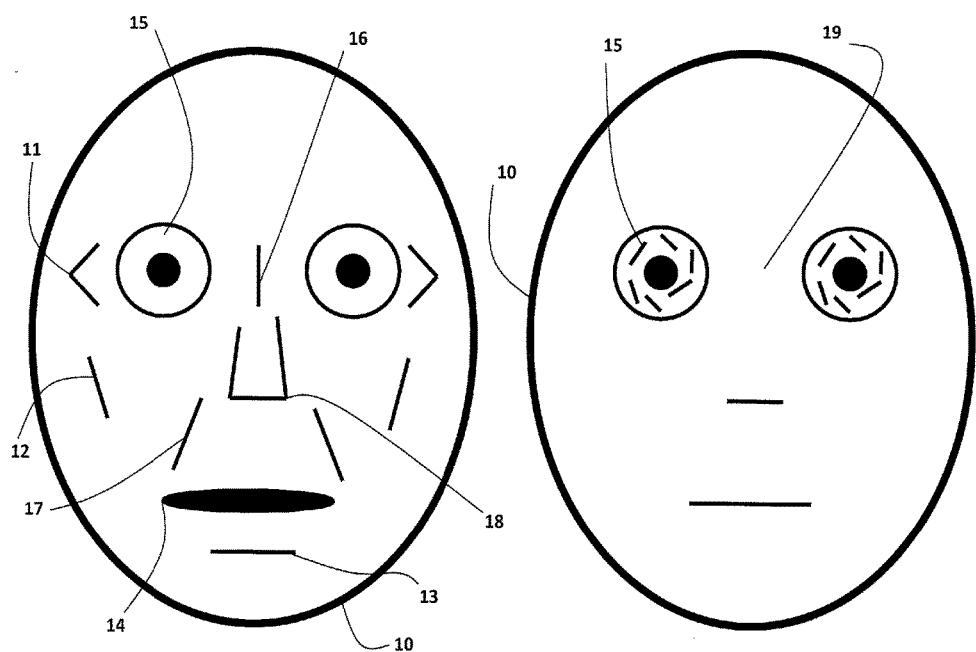

METHOD AND SYSTEM FOR BIOMETRIC RECOGNITION

RELATED APPLICATIONS

This application is a continuation of, and claims priority to U.S. patent application Ser. No. 15/589,752, filed on May 8, 2017, entitled "Method and System for Biometric Recognition", which is a continuation of, and claims priority to U.S. patent application Ser. No. 14/657,415, filed on Mar. 13, 2015, entitled "Method and System for Biometric Recognition", issued as U.S. Pat. No. 9,646,217 on May 9, 2017, which is a continuation of, and claims priority to U.S. patent application Ser. No. 13/787,369, filed on Mar. 6, 2013, entitled "Method and System for Biometric Recognition", which is a continuation of, and claims benefit to U.S. patent application Ser. No. 12/596,019, filed on Oct. 15, 2009, entitled "Method and System for Biometric Recognition" issued as U.S. Pat. No. 8,953,849 on Feb. 10, 2015, which claims priority to International application PCT/US2008/60791, filed Apr. 18, 2008, entitled "Method and System for Biometric System", which claims priority to U.S. provisional application No. 60/925,259, filed Apr. 19, 2007, titled "Method of Improving Performance of Face Recognition Systems", all of which are hereby incorporated by reference in their entireties for all references.

BACKGROUND

This disclosure relates generally to systems and methods wherein imagery is acquired primarily to determine or verify the identity of an individual person using biometric recognition.

Biometric recognition methods are widespread and are of great interest in the fields of security, protection, financial transaction verification, airports, office buildings, but prior to the invention their ability to correctly identify individuals, even when searching through a small reference database of faces or irises, has always been limited, most notably when more than one biometric type is acquired from a single sensor or more generally when poor quality biometric data is acquired. In such cases there are typically false positives (which means that the incorrect person was identified) or false negatives (meaning that the correct person was not identified).

There are several reasons for such poor performance of biometric recognition methods.

First, when comparing a probe face to a reference face, it is important that the biometric templates or features are registered so that corresponding features (nose position for example) can be compared accurately. Even small errors in registration can result in matching errors even if the faces being compared are from the same person.

Second, for facial or iris recognition, it is important that the recognized face or iris and reference face or iris have the same, or very similar, pose. Pose in this context means orientation (pan, tilt, yaw) and zoom with respect to the camera. Variations in pose between the images again results in matching errors even if the faces being compared are from the same person.

Third, the dynamic range or sensitivity of the camera sensor, optical system and digitization system (the Data Acquisition System) may not be sufficient to capture biometric information. For example, some biometric systems are multi-modal, which means that they use several biometrics (for example, iris and face) either to improve the accuracy of recognition or to provide a quality image of the face for human inspection. In such multiple biometric systems and methods there are problems in assuring that each of the sets of data are from the same person, for example the system may unintentionally capture the face of a first individual and iris of a second individual, resulting in an identification or match failure or incorrect association of the face from one person with the iris of another person, for example. Another problem with such multiple biometric systems is difficulty of obtaining good data for each of the separate biometrics, e.g., face and iris because, for example, the albedo or reflectance of one biometric material (the iris for example) may be very different to the albedo of a second biometric (the face for example). The result is that the signal detected of one of the two biometrics is outside the dynamic range or sensitivity of the Data Acquisition System and are either saturated or in the dark current region of the Acquisition System's sensitivity or simply appears as a uniform gray scale with very poor contrast of biometric features, while the second biometric signal is within the dynamic range or sensitivity of the Data Acquisition System and has sufficient signal to noise ratio to enable accurate biometric or manual recognition.

Fourth, the illumination may vary between the images being matched in the biometric recognition system. Changes in illumination can result in poor match results since detected differences are due to the illumination changes and not to the fact that a different person is being matched. In addition, due to the variability in illumination and due to the limited dynamic range or sensitivity of the Data Acquisition System, only some features of the entire biometric (fingerprint or face for example) may be within range of the Data Acquisition System and therefore suitable for biometric matching. This can reduce the number of features available for matching and also greatly reduces biometric accuracy.

Since reflectance of a face is different from that of an iris, acquiring an image of an iris and a face from the same person with a single sensor according to prior methods and systems has yielded poor results. Past practice required two cameras or sensors or, in the cases of one sensor, the sensor and illuminators were operated at constant settings.

For example, Adam, et al., US Pat. Publ. 20060050933 aims to address the problem of acquiring data for use in face and iris recognition using one sensor, but does not address the problem of optimizing the image acquisition such that that the data acquired is optimal for each of the face and iris recognition components separately.

Determan, et al., U.S. Pat. Publ. 20080075334 and Saitoh, et al., U.S. Pat. Publ. 20050270386 disclose acquiring face and iris imagery for recognition using a separate sensor for the face and a separate sensor for the iris. Saitoh claims a method for performing iris recognition that includes identifying the position of the iris using a face and iris image, but uses two separate sensors that focus separately on the face and iris respectively and acquires data simultaneously such that user motion is not a concern.

Determan also discusses using one sensor for both the face and iris, but does not address the problem of optimizing the image acquisition such that that the data acquired is optimal for each of the face and iris recognition components separately.

Jacobson, et al., in US Pat. Publ. 20070206840 also describes a system that includes acquiring imagery of the face and iris, but does not address the problem of optimizing the image acquisition such that that the data acquired is optimal for each of the face and iris recognition components separately.

SUMMARY

We have discovered a method and related system for carrying out the method which captures a high quality image of an iris and the face of a person with single sensor or camera having a sensor by acquiring at least two images with small time elapse between each acquisition by changing the sensor or camera settings and/or illumination settings between the iris acquisition(s) and the face acquisition(s).

The system comprises a sensor, illuminator, and processor adapted to acquire a high quality image of an iris of the person at a first set of parameters. The parameters which can be varied between the first biometric recognition step and the second biometric recognition step, for example between iris and face recognition steps, can include one or more of the following parameters of the Data Acquisition System, by means of example: illumination power setting, camera integration time, wavelengths, frame grabber gain and offset, and frame grabber look-up-table. The acquisitions of the first biometric and the second biometric are within one second of each other, preferably within less than one second of each other. For example, the elapsed time between recognition steps where the parameters are varied can be as little as 0.5, 0.25, 0.1, 0.05, or even less, depending on the capability of the sensor, illuminators, and processor.

The settings on the illuminator and/or sensor are also changed within one second, and within one half, one quarter, or even faster than one tenth of a second, depending on the embodiment.

Some embodiments include the steps of, and related system components or modules for, identifying one or more acquired images containing the iris or face, performing registration over a captured sequence between the identified acquired image, constraining the search for the iris or face in the remainder of the sequence in response to the results of the original identified image, and the recovered registration parameters across the sequence.

Certain embodiments of the invention include determining a distance from the sensor by comparing a diameter of the iris in the iris image with a reference table and/or comparing an separation value between two eyes of the person with a reference table.

The system and method in some cases can adjust focus or zoom as a function of a measured distance between two eyes of the person and/or adjust illumination based on the distance from the sensor, the distance calculated by comparing a diameter of the iris in an iris image with a reference table.

In certain cases the method comprises changing one or more sensor settings of the Data Acquisition System between the acquisition of the face and iris selected from the group consisting of sensor integration time, illumination, shutter speed, aperture, gain and offset of the camera, gain and offset of the frame grabber, and look-up tables in the frame grabber that may select bits of precision that are different from that available from the camera sensor output. The parameters which can be varied between the first image and the second image can be, for example, illumination pulse setting, illumination amplitude setting, camera integration time, camera gain setting, camera offset setting, camera wavelength, and frame grabber settings such as the look-up table.

It is sometimes beneficial for the system to compute the diameter, eccentricity and orientation of the iris upon acquisition of the image of the iris with the sensor, to estimate eye separation, pose of the iris, and/or pose the face.

BRIEF DESCRIPTION OF THE DRAWINGS

The features and advantages of the invention will be appreciated by reference to the detailed description when considered in connection with the attached drawings wherein:

FIG. 1 is a schematic of a face of a person wherein the face features are captured within the dynamic range of the sensor or image grabbing device (the Data Acquisition System) with sufficient contrast for accurate facial recognition, while on the other hand the iris features are captured either outside the dynamic range of the sensor or image grabbing device, or without sufficient contrast for accurate iris recognition.

FIG. 2 is a schematic of the face of the person of FIG. 1 wherein the iris features are captured within the dynamic range of the sensor or image grabbing device and with sufficient contrast for accurate iris recognition, while on the other hand the face features are captured either outside the dynamic range of the sensor or image grabbing device, or without sufficient contrast for accurate facial recognition

DETAILED DESCRIPTION

Figure 3:
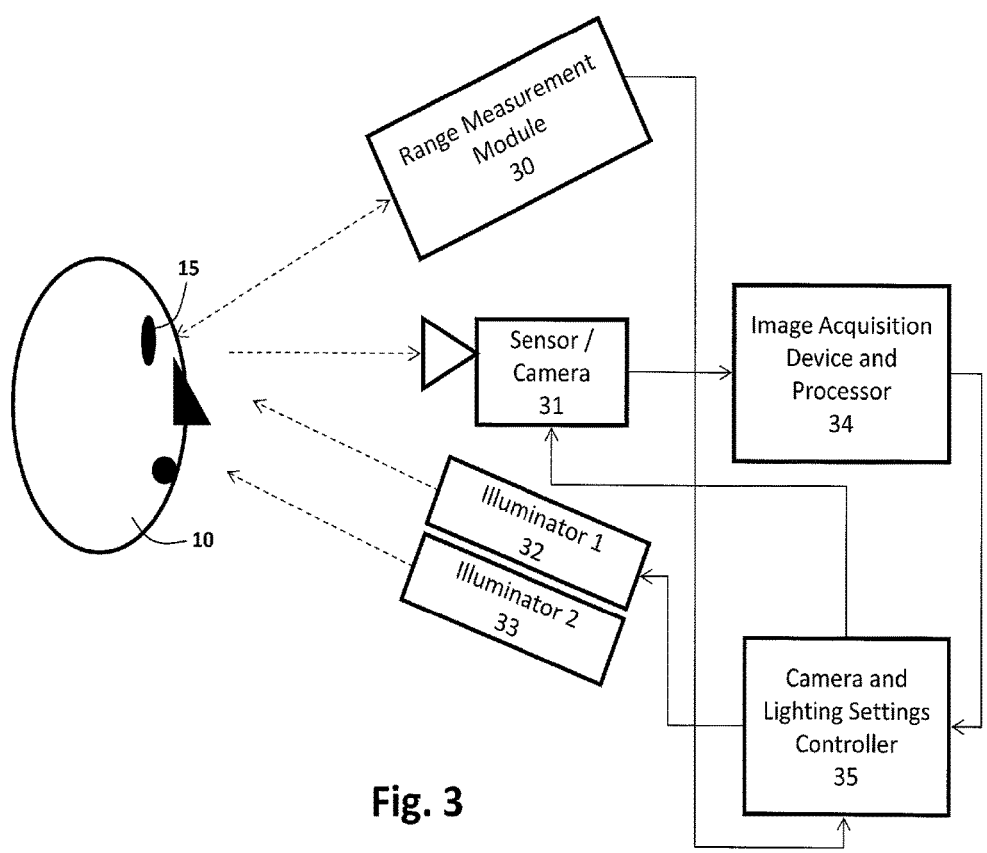
FIG. 3 is a plan view of an image acquisition system comprising a single sensor in a camera and a set of two illuminators.

In the following detailed description, certain embodiments will be illustrated by reference to the drawings, although it will be apparent that many other embodiments are possible according to the invention.

Referring first to FIG. 1, a face 10 is illustrated wherein face features, including corners of eyes 11, wrinkles 12, 13, 16, and 17, and corners of mouth 14 and nose 18 are visible but iris 15 is of low contrast and in poor detail. Such an image could be obtained with low illumination settings with the sensor.

FIG. 2 illustrates the same face 10 as in FIG. 1 but with the iris 15 of high contrast and the face features seen in FIG. 1 not acquired by the sensor but rather the facial features are of low contrast 19.

FIG. 3 is a side view of an embodiment of a system according to the invention wherein a subject 10 is to the left of the figure. Images of the subject are captured by means of the camera 31 and illumination is provided by means of an illuminator or, in the illustrated embodiment, two sets of illuminators wherein first illuminator set 32 are infra-red wavelength illuminators, for example an Axis ACC IR Illuminator model 20812, and second illuminator 33 is a set of Light Emitting Diode (LED) illuminators which have a broad wavelength spectrum, for example Silicon Imaging white LED illuminator 2-61617. In the illustrated embodiment a 2 megapixel resolution CCD camera 31 such as the Aegis PL-B956F model is used with the two sets of illuminators 32, 33. The illumination and camera settings are controlled by the camera and illumination setting controller. The specific parameters controlled by the controller include but are not limited to: camera gain, camera offset, camera integration time, camera look-up table selection, illumination pulse width for illuminator 1, illumination pulse width for illuminator 2, illumination amplitude for illuminator 1, and illumination amplitude for illuminator 2.

An optional range measurement module 30 can also be included. This module 30 measures the approximate distance between the cameras and/or illumination and the subject 10. There are many devices known for measuring range. These include stereo depth recovery methods, such as that described by Horn in "Robot Vision", MIT Press, pages 202-242, or an acoustic/ultrasonic range sensor such as that supplied by Campbell Scientific Inc, model number SR50.

A second method to determine range is to measure the eye separation or iris diameter.

In one embodiment, the system comprises a sensor, lens system, illuminator, and processor adapted to acquire a high quality image of an iris of the person at a first set of illumination power setting, camera integration time, wavelengths and lens settings; and to acquire with the same first sensor a high quality image of the face of the person at a second set of illumination power setting, camera integration time, wavelengths and lens settings, wherein acquisitions of the face image and iris image are within one second of each other, preferably within less than one second of each other.

The settings on the illuminator and/or sensor and/or lens system are also changed within one second, and within one half, one quarter, or even faster than one tenth of a second, depending on the embodiment.

Some embodiments include the steps of, and related system components or modules for, identifying one or more acquired images containing the biometric data, for example the iris or the face, performing registration over a captured sequence between the identified acquired image, constraining the search for the biometric data, including the iris or face, in the remainder of the sequence in response to the results of the original identified image, and the recovered registration parameters across the sequence. The recovered motion between the images may be due to the motion of the person in the scene as they approach or recede from the camera, or may be from motion induced by changes in the lens parameters, such as zooming of the lens or pan and tilt control of the camera.

Certain embodiments of the invention include determining a distance from the sensor by comparing a diameter of the iris in the iris image with a reference table and/or comparing an separation value between two eyes of the person with a reference table.

The system and method in some cases can adjust focus or zoom as a function of a measured distance between two eyes of the person and/or adjust illumination based on the distance from the sensor, the distance calculated by comparing a diameter of the iris in an iris image with a reference table.

In certain cases the method comprises changing one or more sensor and lens settings selected from the group consisting of integration time, illumination, shutter speed, aperture, and gain between the acquisitions of the face and the iris.

It is sometimes beneficial for the system to compute the diameter, eccentricity and orientation of the iris upon acquisition of the image of the iris with the sensor, to estimate eye separation, pose of the iris, and/or pose the face. In one embodiment, the wavelength and brightness of the illumination are varied. More specifically, the camera and illumination parameters are controlled as follows: The visible illuminator 33 is set to provide constant illumination for all acquired frames with a magnitude of 50 milliamps. The remaining IR illuminator 32 is set to a constant pulse width of 6 msecs, but to a pulse magnitude that varies between the two values of 0 milliamps and 400 milliamps between alternate frames that are acquired by the camera. The camera may be set to acquire frames at 3 frames a second The camera integration time may be set at 6 msecs, and the camera gain and offset and camera lookup table may be set to constant values. Those constant values are chosen such that the image of the iris captured when the current is being passed to the Infra-Red illuminator has enough signal to noise for accurate biometric matching. By this embodiment, the images acquired when the current is not being passed to the infrared illuminator are suitable for accurate facial recognition.

In a second embodiment, the camera integration time is varied. More specifically, the camera and illumination parameters are controlled as follows: The visible illuminator is set to provide no illumination for any frame, or a constant illumination for all acquired frames with a magnitude of 50 milliamps. The remaining IR illuminator is set to a constant pulse width of 6 msecs, and to a constant pulse magnitude of 400 milliamps. The camera may be set to acquire frames at 3 frames a second. The camera integration time is set to alternate between adjacent frames between the two values of 1.5 msecs and 6 msecs, and the camera gain and offset and frame grabber lookup table (and other parameters of the Data Acquisition System) may be set to constant values. Those constant values are chosen such that the image of the iris captured when the camera uses the longer integration time has enough signal to noise for accurate biometric matching. In this embodiment, the images acquired when the shorter integration time are suitable for accurate facial recognition.

A third embodiment is the same as the first embodiment, excepting that the magnitude of one or both of the visible illuminators (set at 50 milliamps in embodiment 1) and IR illuminators (set at 400 milliamps in embodiment 1) is adjusted in response to an output of either the processor and/or the depth measurement sensor. More specifically, the processor or range measurement sensor provides an estimate of the range of the subject. This estimate is then used to look-up a preferred intensity magnitude for each of the visible and infra-red illuminators which is then provided to the illuminators. These preferred values are selected by acquiring data from a wide range of subjects under different intensity magnitude settings and at different distances, and by empirically finding the settings that provide the best performance for biometric recognition of the face and iris respectively.

A fourth embodiment first acquires data as described in the first embodiment. In a second step however the images that are optimized for acquiring data of each of the face and iris are aligned using the methods described in this invention, in order to remove any subject or camera motion that may have occurred between the two time instants that each of the optimized data was acquired from the sensor. In this way the features that are optimal for facial recognition in one image can be corresponded to features that are optimal for iris recognition in the other image. This allows processing performed on one image to be used to constrain the results of processing on the other image. For example, recovery of the approximate position and orientation of the face in one image can then be used to constrain the possible position and orientation of the iris in the second image. Similarly, recovery of the position of the iris in one image constrains the possible position of the face in the second image. This can assist in reducing the processing time for one or other of the biometric match processes, for example. In another example, some facial features are most accurately localized and have best signal to noise properties under one set of camera or illumination conditions, whereas another set of facial features are most accurately localized and have best signal to noise properties under another set of camera or illumination settings. This method allows the most accurately localized features of all facial features to be used for facial recognition, thereby providing improved recognition performance. More specifically, the features can be combined by selecting which features from which image have highest signal to noise. There are several methods for feature selection, for example, a contrast measure such as an edge detector can be performed over the image (for example see Sobel, I., Feldman, G., "A 3×3 Isotropic Gradient Operator for Image Processing", Pattern Classification and Scene Analysis, Duda, R. and Hart, P., John Wiley and Sons, '73, pp 271-272), and the magnitude of the result can be used to select the feature from either image with the largest contrast.

The image resolution typically required for face recognition is recognized to be approximately 320×240 pixels, as documented in an ISO standard. As part of the image acquisition system, however, we use a camera capable of imaging the face with a much higher resolution, for example 1024×1024 pixels. This higher resolution data enables the detection and localization of features that cannot be detected reliably in the lower resolution data, and also enables more precise and robust detection of features that could be seen in the lower resolution imagery. For example, the precise location of the pupil boundary can be recovered in the high resolution imagery and typically cannot be recovered accurately in the lower resolution imagery. One method for detecting the pupil/iris boundary is to perform a Hough transform, for example. U.S. Pat. No. 3,069,654. The face recognition algorithm may use the same high resolution data that is being captured or by using an additional low resolution camera. An additional method for performing registration is to perform alignment algorithms over the eye region. In this case the eye region in one face image is aligned to sub-pixel precision to the eye region in another face image. Registration can also be done over the entire image or over the face region. Registration can be performed for example by methods described in Horn, "Robot Vision", MIT Press p 278-299. The precise localization information can be passed to the face recognition algorithm in order to improve its performance.

In addition to eye location, the image acquisition system also recovers the zoom or distance of the person. This is accomplished by setting the high resolution camera to have a very narrow depth of field. This means that features of the face only appear sharply in focus at a specific distance from the camera. Methods can be performed to detect when those features are sharply in focus, and then only those images are selected for face recognition. If a second lower resolution camera is used for acquiring the data used for face recognition, then processing performed on the high-resolution imagery to detect sharply-focused features is used to trigger image acquisition on the lower resolution camera. This ensures that the face images used for face recognition are all at the identical scale. There are several methods available to detect sharply-focused features. For example, an edge filter can be performed over the image (see Sobel, I., Feldman, G., "A 3×3 Isotropic Gradient Operator for Image Processing", Pattern Classification and Scene Analysis, Duda, R. and Hart, P., John Wiley and Sons, '73, pp 271-272) and then squared at each pixel, and then averaged over the image in order to compute an edge energy score. When the score is maximal or exceeds a threshold, then the person is within the depth of field of the high resolution camera.

Knowledge of the eye location as well as the zoom of the face allows specific sub-regions of the face to be selected and used for face recognition. For example, one or more rectangular regions of a certain size (in pixels) can be cut out from the high-resolution imagery and used as an input to a face recognition engine, even though only part of the face is being presented. The locations of certain areas, such as the nose, can be predicted using a model of a standard face, and using knowledge of the eye location and the zoom. The face recognition engine is informed that only one or more specific subsets of the face are being presented. In this case we only provide a face recognition database to the face recognition engine that comprises only the same specific subset regions.

If a second camera is used to acquire data for face recognition (or any other biometric recognition, such as ear recognition) then because the location of the first camera is different to that of the second camera, then recovering a precise pixel location in the first camera does not simply translate into a corresponding pixel location in the second camera. We accomplish this using knowledge of the location of the depth of field of the first camera, which in turn provides a very precise depth of the face with respect to the first camera. Given a pixel location in the first camera, and the depth of the person, as well as camera intrinsics (such as focal length, and relative camera translation) that can be calibrated in advance (see for example, "An Efficient and Accurate Camera Calibration Technique for 3D Machine Vision", Roger Y. Tsai, Proceedings of IEEE Conference on Computer Vision and Pattern Recognition, Miami Beach, F L, 1986, pages 364-374), then it is known how to compute the precise pixel location of the corresponding feature in the second camera (see Horn, "Robot Vision", MIT Press, p 202-242 for example).

In addition to ensuring consistent zoom, we also take steps to ensure consistent pose by detecting features in the high-resolution image that would not otherwise be visible with precision in the low resolution imagery. For example, the pupil boundary is only near-circular if the person is looking in the direction of the camera. A method for detecting circular or non-circular boundaries is the Hough Transform, for example see U.S. Pat. No. 3,069,654. If imagery of the iris is near circular in the narrow field of view imagery, then imagery of the face is in the lower resolution camera is more likely to be of a frontal view and is passed to the facial recognition module. Similarly, the pose of the face can be recovered and used to constrain the expected pose of the iris for subsequent processing.

The image acquisition system also has a dynamic range control module. This module addresses the problem where data from two different biometrics (e.g. iris and face) cannot be reliably acquired because the dynamic range of the sensor, and the Data Acquisition System in general, is limited. We address this by two methods.

First, we acquire data at two different but controlled times in such a way that at the first time instance we expect that the first biometric imagery (e.g., face) imagery will be within the dynamic range of the sensor given the specific illumination configuration. We then acquire data at a second time instance where we expect the second biometric imagery (e.g. iris imagery) to be within the dynamic range or sensitivity of the sensor. For example, consider a configuration where a camera and an illuminator lie close to each other, and a person is approaching the configuration. Images are continuously captured. As the person approaches the configuration, then the reflectance off the biometric tissue (face or iris) increases since the distance from the person to the camera and illumination configuration is decreasing. At one distance it can be expected that data corresponding to one biometric will be within the dynamic range (e.g. face) while at a different distance, it can be expected that data corresponding to a second biometric can be within the dynamic range (e.g. iris). The camera may have a small depth of field due to the resolution requirements of obtaining one biometric (e.g. the iris). However, the resolution required for the other biometric may be much coarser so that blurring due to imagery lying outside the depth of field has negligible impact on the quality of data acquired for the other biometric (e.g. the face).

A specific implementation of this approach is to a) Acquire all images into a stored buffer, b) detect the presence of an eye in the depth of field of the camera using the methods described earlier, c) compute the number of frames back in time where the person was situated at a further distance from the depth of field region (and therefore illuminated less), based on a prediction of their expected motion (which can be, for example, a fixed number based on walking speed), and d) select that imagery from the buffer to be used for face recognition. The eye and face location can be registered over time in the buffer to maintain knowledge of the precise position of the eyes and face throughout the sequence. Registration can be performed for example by Horn, "Robot Vision", MIT Press p 278-299

The second method for ensuring that data lies within the dynamic range of the camera is to modulate the magnitude of the illumination over a temporal sequence. For example, in one frame the illumination can be controlled to be much brighter than in a subsequent frame. In one implementation, images are always acquired at a low illumination level suitable for one biometric. Features are detected that would only be observed when the face is fully in focus and within the depth of field region. For example, the Sobel image focus measure previously cited can be used. When the face is near or within the depth of field region, based for example on a threshold of the focus measure, then the illumination can be increased in order to obtain imagery of the second biometric (e.g. the iris) within the dynamic range of the camera. When the face has left the depth of field region, then the illumination can revert back to the lower magnitude level.

In addition to modulating the magnitude of the illumination, we also modulate the wavelength of the illumination. This allows multiple datasets corresponding to the same biometric to be acquired and matched independently, but using the constraint that the data belongs to the same person. For example, person A may match dataset B and C using data captured at one wavelength, but person A may match dataset C and D using data captured at a second wavelength. This gives evidence that person A matches to dataset C. This approach is extended to not only include fusing the results of face recognition after processing, but also by including the multi-spectral data as a high dimensional feature vector as an input to the face recognition engine.

In some embodiments there is an advantage to aligning the acquired images of the face and iris with the processor, thereby reducing the effect of camera or subject motion that may have occurred between the two time instants that each of the images was acquired from the sensor. In this way the features that are optimal for facial recognition in one image can be corresponded to features that are optimal for iris recognition in the other image. This allows processing performed on one image to be used to constrain the results of processing on the other image. For example, recovery of the approximate position and orientation of the face in one image can then be used to constrain the possible position and orientation of the iris in the second image. Similarly, recovery of the position of the iris in one image constrains the possible position of the face in the second image. This can assist in reducing the processing time for one or other of the biometric match processes, for example. In another example, some facial features are most accurately localized and have best signal to noise properties under one set of camera or illumination conditions, whereas another set of facial features are most accurately localized and have best signal to noise properties under another set of camera or illumination settings. This method allows the most accurately localized features of all facial features to be used for facial recognition, thereby providing improved recognition performance.

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

I claim:

1. A system for acquiring iris and face biometric features, the system comprising:
    a depth measurement sensor configured to determine a distance of an image sensor from a subject;
    at least one light source; and
    the image sensor, the image sensor configured to:
        acquire, at a first time instant, a first image comprising a biometric feature of a face of the subject, the face illuminated by light of a first wavelength from the at least one light source set to a first intensity magnitude suitable for acquiring the first image at the determined distance; and
    acquire, at a second time instant, a second image comprising a biometric feature of an iris of the subject, the iris illuminated by light of a second wavelength from the at least one light source set to a second intensity magnitude suitable for acquiring the second image at the determined distance, wherein the second time instant is within a predetermined time period of the first time instant sufficient to link the first image and the second image to the same subject.

2. The system of claim 1, wherein the depth measurement sensor is configured to determine the distance of the image sensor from the subject by determining at least one of a diameter of the iris or a separation distance between two eyes of the subject.

3. The system of claim 1, further comprising at least one processor configured to perform biometric recognition using the first image comprising the biometric feature of the face, and perform biometric recognition the second image comprising the biometric feature of the iris.

4. The system of claim 1, further comprising at least one processor configured to determine an orientation of the face using the first image, and determine an expected orientation and location of the iris on the second image using the determined orientation of the face.

5. The system of claim 1, further comprising at least one processor configured to perform registration between the first image comprising the biometric feature of the face and the second image comprising the biometric feature of the iris.

6. The system of claim 1, wherein the at least one light source comprises a visible light illuminator configured to provide the light of the first wavelength, and an infra-red light illuminator configured to provide the light of the second wavelength.

7. The system of claim 1, further comprising at least one processor configured to adjust at least one of the light of the first wavelength or the light of the second wavelength responsive to the determined distance.

8. The system of claim 1, wherein the depth measurement sensor is configured to determine the distance by comparing at least one of a diameter of the iris or a separation distance between two eyes of the subject, with one or more values of a reference table.

9. The system of claim 1, further comprising an imaging controller configured to adjust at least one of: sensor gain, sensor offset, illumination pulse width, shutter speed, focus, zoom or integration time for image acquisition, between the acquisition of the first image and the acquisition of the second image.

10. The system of claim 1, wherein the image sensor is configured to acquire at least one of the first image or the second image while the subject is in motion.

11. A method for biometric acquisition, the method comprising:
   determining, by a depth measurement sensor, a distance of an image sensor from a subject;
   acquiring, by the image sensor at a first time instant, a first image comprising a biometric feature of an iris of the subject, the iris illuminated by light of a first wavelength set to a first intensity magnitude suitable for acquiring the first image at the determined distance; and
   acquiring, by the image sensor at a second time instant, a second image of a biometric feature of a face of the subject, the face illuminated by light of a second wavelength set to a second intensity magnitude suitable for acquiring the second image at the determined distance, wherein the second time instant is within a predetermined time period of the first time instant sufficient to link the first image and the second image to the same subject.

12. The method of claim 11, wherein determining the distance of the image sensor from the subject comprises determining at least one of a diameter of the iris or a separation distance between two eyes of the subject.

13. The method of claim 11, further comprising performing biometric recognition using the first image comprising the biometric feature of the iris, and performing biometric recognition using the second image comprising the biometric feature of the face.

14. The method of claim 11, further comprising determining an orientation of the face using the second image, and determining an expected orientation and location of the iris on the first image using the determined orientation of the face.

15. The method of claim 11, further comprising performing registration between the first image comprising the biometric feature of the iris and the second image of the biometric feature of the face.

16. The method of claim 11, wherein the light of the second wavelength is provided by a visible light illuminator and the light of the first wavelength is provided by an infra-red light illuminator.

17. The method of claim 11, further comprising adjusting at least one of the light of the first wavelength or the light of the second wavelength responsive to the determined distance.

18. The method of claim 11, wherein determining the distance comprises comparing at least one of a diameter of the iris or a separation distance between two eyes of the subject, with one or more values of a reference table.

19. The method of claim 11, further comprising adjusting, by an imaging controller, at least one of: sensor gain, sensor offset, illumination pulse width, shutter speed, focus, zoom or integration time for image acquisition, between the acquisition of the first image and the acquisition of the second image.

20. The method of claim 11, wherein the acquisition of at least one of the first image or the second image occurs while the subject is in motion.

* * * * *